United States Patent
Gorhan et al.

(10) Patent No.: US 9,717,434 B2
(45) Date of Patent: Aug. 1, 2017

(54) PERFUSION CANNULA WITH INTEGRATED SENSOR TECHNOLOGY

(71) Applicant: Novalung GmbH, Heilbronn (DE)

(72) Inventors: Holger Gorhan, Schönaich (DE); Thomas Hartig, Heilbronn (DE)

(73) Assignee: Novalung GmbH, Heilbronn (DE)

( * ) Notice: Subject to any disclaimer, the term of this patent is extended or adjusted under 35 U.S.C. 154(b) by 208 days.

(21) Appl. No.: 14/338,213

(22) Filed: Jul. 22, 2014

(65) Prior Publication Data
US 2015/0031977 A1  Jan. 29, 2015

(30) Foreign Application Priority Data
Jul. 24, 2013 (EP) .................................. 13003716

(51) Int. Cl.
| | | |
|---|---|---|
| A61B 5/042 | (2006.01) | |
| A61B 5/0215 | (2006.01) | |
| A61B 5/00 | (2006.01) | |
| A61M 1/36 | (2006.01) | |
| A61M 25/00 | (2006.01) | |

(52) U.S. Cl.
CPC .......... *A61B 5/042* (2013.01); *A61B 5/02154* (2013.01); *A61B 5/0422* (2013.01); *A61B 5/6866* (2013.01); *A61M 1/3659* (2014.02); *A61B 2562/0209* (2013.01); *A61B 2562/223* (2013.01); *A61M 2025/0002* (2013.01); *A61M 2205/3344* (2013.01); *A61M 2230/04* (2013.01)

(58) Field of Classification Search
CPC ..... A61B 5/042; A61B 5/0422; A61B 5/0215; A61B 5/02152; A61B 5/02154; A61B 5/02158
See application file for complete search history.

(56) References Cited

U.S. PATENT DOCUMENTS

| | | | |
|---|---|---|---|
| 5,029,585 A | 7/1991 | Lieber et al. | |
| 5,065,010 A | 11/1991 | Knute | |
| 5,433,742 A | 7/1995 | Willis | |
| 5,701,905 A * | 12/1997 | Esch | A61B 5/0215 600/486 |
| 7,787,963 B2 * | 8/2010 | Geistert | A61M 25/0662 600/374 |
| 2002/0111662 A1 | 8/2002 | Iaizzo et al. | |
| 2011/0295177 A1 | 12/2011 | Mohl | |
| 2013/0012923 A1 * | 1/2013 | Baxter | A61B 18/1492 604/523 |

FOREIGN PATENT DOCUMENTS

EP  0 127 476 A2  12/1984

* cited by examiner

*Primary Examiner* — Lee S Cohen
(74) *Attorney, Agent, or Firm* — Seed Intellectual Property Law Group LLP (57) ABSTRACT

The present invention relates to a perfusion cannula for placement of an access, having a cannula wall and a perfusion lumen which is surrounded by the cannula wall and in which a fluid flow can flow through the perfusion cannula, wherein the perfusion cannula furthermore comprises at least one sensor lumen and at least one sensor device, in particular an ECG sensor, which is arranged at least partially in the sensor lumen. As a result, it is possible to provide a particularly reliable perfusion cannula with improved functionality and for reliable handling, in particular in conjunction with an extracorporeal lung support system.

24 Claims, 5 Drawing Sheets

PERFUSION CANNULA WITH INTEGRATED SENSOR TECHNOLOGY

BACKGROUND

Technical Field

The invention relates to a perfusion cannula according to the preamble of Claim 1 for placement of an arterial or venous access, in particular in connection with circulation replacement therapy.

BRIEF SUMMARY

Circulation replacement therapy can take place for example by means of an extracorporeal lung support system, by means of which blood, or a blood-replacing fluid, is removed from a patient at one point (in particular venously) and replaced at another point (in particular arterially) after it has been enriched with oxygen and/or its carbon dioxide content has been lowered. To this end, so-called membrane ventilators can be used, which are also known as membrane oxygenators. The blood/fluid can be removed and supplied by means of cannulas.

The term "perfusion" here refers to the supply of organs with blood. An organ perfusion takes place naturally by way of arteries and veins, although it can also take place artificially, for example by way of bypasses or extracorporeal lines which can be connected to the organism by means of perfusion cannulas. Perfusion cannulas are often used for arterial puncture, but also as venous perfusion cannulas. They provide a supply channel through which a fluid (e.g. blood or a blood substitute) can be supplied or removed. Perfusion cannulas are used for example when a person or animal is in a shock situation. In shock situations, it is also very important that the vital state is monitored.

To enable evaluation of the vital state of a person or animal, it is on the one hand important to check the heart function. This can take place by electrically recording the electrical activity of the heart muscle. This can generate an electrocardiogram, i.e. a record of the electrical activity of the heart. The electrocardiogram is normally generated by way of an impedance measurement using (adhesive) electrodes applied to the skin of the person/animal (henceforth "patient"). An ECG measurement here is made more difficult for example due to high skin resistance or as a result of adhesive electrodes which only adhere inadequately to the skin (in particular owing to the skin being damp). There is also the risk of the skin being damaged by the electrodes. The measurement is also made more difficult in that the electrodes can slip, which can be a significant problem if the patient puts up resistance or is in an unstable position.

A further important measurement relates to the blood pressure of the patent. A blood-pressure measurement can take place for example invasively, in that a pressure in one of the peripheral arteries of the patient, e.g. an arm or leg artery, is recorded by means of a cannula. A pressure measurement requires a separate pressure measurement system in which the pressure is recorded by way of a water column for a pressure measurement system and is supplied to a monitoring system for checking vital functions and for diagnosis, respectively, of the patient. In the case of a peripheral vasoconstriction (vascular obstruction), in particular in a shock situation of the patient, the necessary cannulation for this pressure measurement can mostly only be placed with difficulty, since the preferred points for this at the wrists or elbows are greatly restricted or since groin vessels are unavailable due to extracorporeal processes.

It is an object of the invention to provide a perfusion cannula which overcomes the above-mentioned disadvantages, in particular a perfusion cannula with improved functionality, e.g. in shock situations of a patient who is to be treated or examined. The perfusion cannula should preferably enable reliable handling and/or be able to fulfil functions in particularly reliable manner. The device here should more preferably also be robust with regard to disturbing influences.

At least one of the above-mentioned objects is achieved by a perfusion cannula according to Claim 1.

In the following figures, the invention is explained in more detail by means of exemplary embodiments, whereby different arrangements of sensor lumina are demonstrated.

DETAILED DESCRIPTION

The invention starts with a perfusion cannula for placement of an access, having a cannula wall and a perfusion lumen which is surrounded by the cannula wall and in which a fluid flow can flow through the perfusion cannula.

According to the invention, it is provided for the perfusion cannula to furthermore comprise at least one sensor lumen and at least one sensor device, in particular an ECG sensor, which is arranged at least partially in the sensor lumen. As a result of this, it is also possible to record vital parameters by means of the sensor device, in particular (blood) pressure and/or the electrical activity of the heart or electrocardiogram, respectively, whereby the vital parameters can be recorded within the body of the patient, in particular in the direct vicinity of the heart. The vital parameters can therefore even be reliably recorded in the event of a shock situation of the patient in which there is a narrowing (vasoconstriction) of peripheral, distal vessels of the patient.

Only a single cannulation is necessary here, in particular a femoral cannulation (in the thigh or groin area). By means of the perfusion cannula, it is for example possible for venoarterial circulation support to take place or a triggered diastolic augmentation (increase in blood pressure) or generally a therapy in any type of shock situation (in particular cardiac, septic, traumatic) or resuscitation. It is possible to monitor vital functions simultaneously during this.

The sensor device is preferably positioned in fixed manner in relation to a (free) distal end of the perfusion cannula in the sensor lumen. The position of the sensor device relative to the patient is thereby specified by the position of the perfusion cannula, in particular the distal end thereof. The sensor device is particularly preferably cast or embedded in the cannula wall.

A perfusion cannula here is preferably understood to be a device which is designed for placement of an access to a vessel or organ for extracorporeal circulation and through which a fluid can be supplied or removed. The access here can be an arterial or venous access; the perfusion cannula is preferably placed for femoral arterial access in a groin area of the patient.

A distal end here is preferably understood to be an end of the perfusion cannula which faces away from an operator or surgeon, respectively, and towards the patient, i.e. the end which has to be introduced into the patient. The cannula geometry is preferably designed here so that the transitions at the tip of the cannula are as small as possible. The transitions are preferably smaller than 0.1 mm.

The sensor lumen can optionally be constructed as a recess, opening, cutout or bore passing through the perfusion cannula in the longitudinal direction or it can be sealed off in the region of a distal end of the perfusion cannula, in particular after an appropriate sensor device has been arranged in a suitable position fixed in the sensor lumen. The sealing-off here can itself also fix and support the sensor device in the sensor lumen. The sensor lumen is preferably circular in cross-section. Hereby a sensor device can be guided easily through the sensor lumen without colliding with edges or undercuts. The sensor lumen optionally has an elliptical or other circular inner lateral surface with continuous transitions, in particular corresponding to a cross-sectional geometry of a corresponding sensor device.

It is possible here to produce one or more sensor lumina together with the cannula wall in each case by way of a dip and rotate procedure. This can be carried out by applying polymers in layers, comparable to candle dipping or by means of a metering device on a rotating workpiece carrier. By way of example, a reinforcing wire, a cable or other components can be incorporated during this.

According to one variant, the sensor lumen is formed during the manufacturing process (e.g. extrusion) by a cavity, corresponding to a placeholder, which is incorporated in the cannula wall. It is therefore possible to provide a sensor lumen at a freely selectable position in the cannula wall and the number of sensor lumina can be freely selected as required, in particular also after the cannula wall of the perfusion cannula has already been manufactured. A sensor lumen can be manufactured here in association with extrusion, or with a placeholder which is removed after the manufacture, or by incorporating prefabricated hollow bodies.

According to a preferred embodiment, the sensor lumen is integrated in the cannula wall or arranged on the cannula wall, protruding laterally in the radial direction, in particular protruding inwardly into the perfusion lumen. An integrated sensor lumen can ensure that the function of the perfusion cannula for removing or supplying the fluid is not impaired. A sensor lumen protruding inwardly into the perfusion lumen can ensure that sensor devices which have a greater diameter than the wall thickness of the cannula wall can also be used in conjunction with the perfusion cannula. An arrangement laterally inside at the cannula has the advantage of being simple to manufacture or also having good flow properties, in particular since the cannula wall can be of a thinner construction and it is thereby possible to achieve higher flow rates for a particular external diameter of the cannula.

A sensor lumen which is integrated in the cannula wall is thereby understood to be a lumen which is provided within the cannula wall without the cannula wall being provided with a particular geometry for this which deviates from the actual cannula wall geometry. If the cannula wall is constructed for example as a hollow cylindrical body, the sensor lumen is provided between the two cylindrical lateral surfaces without having to deviate from the cylindrical geometry. A sensor lumen which is integrated in the cannula wall therefore has a diameter which is smaller than the thickness of the cannula wall.

The cannula wall is preferably constructed with an at least approximately cylindrical inner side (in particular a continuous inner lateral surface). The cannula wall is more preferably constructed with an at least approximately cylindrical outer side (in particular a continuous outer lateral surface). This results, in particular when both lateral surfaces are arranged concentrically, in isotropic bending properties and rigidities of the perfusion cannula. With this cross-sectional geometry, it is also readily possible to design the diameter of the perfusion cannula so that it is variable along the longitudinal extent of the perfusion cannula, in particular in the case of a tapering perfusion cannula.

According to a preferred embodiment, the perfusion cannula has an insertion length of greater than 15 cm, preferably greater than 20 cm, more preferably greater than 25 cm, in particular in the range of 25 to 50 cm. This enables the provision of an arterial perfusion cannula which can also be inserted into a groin region of a patient and whereof the distal end can reach the vicinity of the heart of the patient.

The insertion length here is understood to be the length of the portion of the perfusion cannula which can be inserted maximally into a patient. In the case of an arterial perfusion cannula, the insertion length is preferably considerably greater than 25 cm and is for example in the range of 45 to 50 cm. The perfusion cannula preferably has a coating with good gliding properties on tissue surfaces, at least over the insertion length. The coating can be a polyurethane coating.

The perfusion cannula preferably has a total length in the range of 20 to 100, more preferably 25 to 75 cm. The total length here is understood to be the length of the perfusion cannula from a distal end (cannula tip) to a proximal end, whereby the perfusion cannula can be coupled at the proximal end to a console, in particular an evaluating unit. The total length is greater than the insertion length, so that an operator or surgeon, respectively, is able to handle the perfusion cannula in any case, even when it has been inserted over the maximum insertion length. The total length is preferably at least 10 cm, preferably at least 15 cm, greater than the insertion length.

The perfusion cannula here is preferably constructed as an arterial perfusion cannula for insertion into an artery. Such an arterial perfusion cannula preferably has no radial cutouts or holes in the cannula wall, but only has an opening at the distal end, by way of which blood or another fluid can be supplied to a patient. However, radial cutouts or holes in the cannula wall can be provided in venous perfusion cannulas, in particular for enabling a larger quantity of blood or fluid to be removed from a patient per unit of time (increasing the drainage capacity), in particular so that it is also possible to reduce the strain on the heart. In the case of venous perfusion cannulas, for example ten radial cutouts or holes can be provided, in particular in a distal region of the perfusion cannula, to enable blood/fluid to be withdrawn directly at the heart, in particular directly from the atrium of the heart or the precava (superior vena cava). Optionally, the arterial perfusion cannula can also have one or two small radial holes or cutouts, albeit considerably fewer or smaller holes than a venous perfusion cannula. This enables blood to be supplied not only to the cannula tip but also laterally thereof. It is also possible to ensure good perfusion of abdominal organs and lower flow velocities can be established. The holes preferably have a diameter of 0.5-5 mm, more preferably 1-3 mm.

According to a preferred embodiment, in the region of a distal end of the perfusion cannula, the perfusion cannula has an external diameter of between 5 and 35 French (Fr) corresponding approximately to 1.7 and 11.7 mm, preferably between 12 and 25 French (Fr) corresponding approximately to 4 and 8.4 mm. This enables the provision of a particularly narrow, thin and flexible perfusion cannula, which can also assume a diagnostic function. The strain on the patient is no greater with the perfusion cannula according to the invention than with a conventional cannula, in particular because an incision for inserting the perfusion cannula can remain small despite the additional sensor device(s).

The region of a distal end is here understood to be a portion of the perfusion cannula which extends over a length of a maximum of 5 cm, preferably a maximum of 3 cm, from a distal end of the perfusion cannula in the proximal direction.

Preferably, the wall thickness of the perfusion cannula along the entire insertion length is less than 2 mm, preferably less than 1 mm, more preferably less than 0.5 mm. This enables the provision of a perfusion cannula, in particular an arterial perfusion cannula, which, in spite of a significant length, is flexible and can be easily handled and can be advanced from a groin area to the heart of a patient.

In the region of a proximal end of the perfusion cannula, the perfusion cannula preferably has an external diameter of between 5 and 35 French, preferably between 12 and 25 French. This enables the provision of a proximal end which is stable so that a cannula tip can also be pushed through an artery or vein over a longer insertion length. The perfusion cannula preferably tapers in the insertion portion, in particular continuously over the insertion length. The taper here is preferably provided in a connector region of the perfusion cannula or is particularly pronounced. The external diameter is preferably constant in the region of the insertion length. A tapering is preferably present at the cannula tip.

According to a preferred embodiment, at least one of the at least one sensor device is constructed as an ECG sensor. The (ECG) sensor lumen can have a diameter of between 0.05 and 2 mm, preferably 0.2 and 0.5 mm. The ECG sensor here can substantially be formed by two electrodes and lines electrically contacting the electrodes. This enables an ECG measurement to be carried out by means of a particularly small sensor which can be guided in the sensor lumen. An internal diameter of the sensor lumen which is matched to the external diameter of the ECG sensor facilitates the assembly of the ECG sensor in the perfusion cannula. For example, the ECG sensor can be prevented from tilting in the sensor lumen. This enables the provision of a thin cannula wall with good flexibility (good elastic properties) which has good stability in spite of the sensor lumen. With a small wall thickness, the pressure loss is only slight.

Such a perfusion cannula with an ECG sensor can be provided for an arterial ECG measurement, i.e. an ECG measurement in which the perfusion cannula is introduced through an artery into the vicinity of the heart of a patient, in particular by way of the groin area, without having to surgically open the thoracic or abdominal region of the patient, for example. The ECG sensor is preferably constructed measuring bipolarily. The ECG sensor can be connected to an evaluating unit by a proximal end, for example by way of a tension-resistant plug connection.

According to a preferred embodiment, the at least one of the at least one sensor device is constructed as an ECG sensor and has an annular electrode which is arranged externally around the cannula wall and is electrically contacted by an electrical conductor guided in the corresponding sensor lumen. This enables the provision of an ECG sensor by means of which the electrodes can be brought particularly close to the region of the heart. This enables a precise measurement. The choice of material for the perfusion cannula can take place largely independently of the electrical function of the electrodes. The electrodes can be electrically insulated with respect to the cannula. Furthermore, the measurement is not dependent on a rotation of the perfusion cannula about a central longitudinal axis, since the annular electrodes are of a circumferential construction and can carry out a measurement in all directions of a plane which is perpendicular to the central longitudinal axis. As a result, the ECG measurement can be handled particularly simply and reliably. A reliable measurement can always be ensured, regardless of the state of the patient or the orientation of the perfusion cannula. The electrode preferably consists of a biocompatible material.

The annular electrode can be connected directly to an electrical line which is guided through the sensor lumen and can be connected to an evaluating unit. The electrical line can be for example a 3-5 pole cable. The annular electrode can also optionally be coupled to a further part of the ECG sensor device, which is in turn coupled to the evaluating unit, in particular by way of an electrical line. The electrical line can be embedded in the sensor lumen.

The electrode or annular electrode, respectively, is preferably a passive electrode which is coupled to a line (a line leading away from the electrode). For example, 3-5 pole lines or cables, respectively, can be provided.

The perfusion cannula preferably has two electrodes or annular electrodes which are arranged at a predetermined distance from one another, in particular in the range of 5 to 200 mm, preferably 30 to 80 mm. As a result, it is possible to record the electrical activity of the heart or the electrocardiogram, respectively, with great accuracy, particularly since the electrodes are always arranged at a predefined distance from one another. It is possible to prevent faulty operation, such as, for example, the electrodes not being adhered to the chest in the optimal position.

According to a preferred embodiment, the at least one of the at least one sensor device is constructed as an ECG sensor with two electrodes arranged inside of the sensor lumen. This enables the provision of a perfusion cannula which is particularly easy to manufacture. Electrical feedthroughs leading outwards are not required. The perfusion cannula here can be constructed with an at least substantially planar outer lateral surface with no edges, bumps or breaks, so that the perfusion cannula on the one hand has constant bending properties in relation to its central longitudinal axis and on the other can also be shifted in an artery or vein with little resistance.

The electrodes or annular electrodes are preferably positioned at a predetermined distance from a distal end of the perfusion cannula. This enables a positioning of the electrodes to take place by a position of the distal end of the perfusion cannula. The distal end here can be arranged in the aortic arch of the thoracic aorta (in the chest region), with the distance of the electrodes from the distal end being specified in such a way that the electrodes are arranged in a position relative to the heart which is expedient for technical measuring purposes.

According to a preferred embodiment, at least one of the at least one sensor device is constructed as a pressure sensor. Preferably, thereby at least two sensor lumina are provided and an ECG sensor is arranged in the other sensor lumen. This enables several vital parameters to be recorded rapidly and efficiently and only a single vessel access is required here, in particular an arterial access. The perfusion cannula can be used for recording both electrical activity of the heart or the electrocardiogram, respectively, and also blood pressure. Thereby, also only a single cannulation is required for recording at least two vital parameters. The risk of disturbing influences can be reduced, in particular because it is possible to take in vivo measurements. It is also possible to record further vital parameters, in particular blood pressure, in the direct vicinity of the heart. The cannula here can be used (in particular simultaneously) on the one hand for measuring the vital parameters and, on the other, for extracorporeal circulation as a perfusion cannula without any particular limitation. The cannula wall is merely of a somewhat thicker construction than for a conventional perfusion cannula and is possibly somewhat more rigid.

Preferably, the sensor lumen is integrated in the cannula wall for the purpose of receiving the pressure sensor. It is possible here for not only two, but also further sensor lumina to be provided, for example three to five sensor lumina.

According to a preferred variant, the sensor lumina are arranged concentrically around a central longitudinal axis of the perfusion cannula. A perfusion cannula can therefore be provided in which the selection of a particular sensor lumen for a particular sensor does not influence the measurement, i.e. it is not necessary to take into account the arrangement of the sensor in the cannula relative to the cannula wall when taking a measurement, in particular because the lumina are arranged at the same distance from an outer lateral surface of the perfusion cannula. This also facilitates the manufacture of the perfusion cannula, in particular when there is a large number of sensor lumina, e.g. five sensor lumina. The sensor lumina are preferably arranged such that they are distributed over the circumference at a uniform spacing from one another and therefore arranged symmetrically in relation to the total circumference. This enables the provision of a perfusion cannula which has the same bending rigidity about its central longitudinal axis in all spatial directions, at least when the sensor lumina have the same (internal) diameter, and can therefore be handled more easily.

Preferably, the cannula wall is constructed in an annular shape in cross-section and has a width or wall thickness, respectively, of less than 2 mm, preferably less than 1 mm, more preferably less than 0.5 mm. This enables the provision of a perfusion cannula with a cannula wall as narrow as possible, which is flexible and can also be bent in the same manner in all spatial directions.

According to a preferred embodiment, the pressure sensor is constructed as a fibre optic pressure sensor. This enables the provision of a particularly compact pressure sensor which can be expediently integrated in a small lumen of a perfusion cannula without making the perfusion cannula noticeably more difficult to handle. The measurement can be carried out without fluids, it can be carried out with greater measuring accuracy and the measurement has a low susceptibility to faults. Optionally a measurement can be carried out by way of a water column.

Preferably, at least one sensor lumen is provided for a fibre optic pressure sensor and constructed as a channel which is open on both sides. The pressure sensor can be housed for example in an embedding medium (in particular a transparent polymer) which can also ensure a sealing action. It is also separately or additionally possible for a sealing-off to be optionally formed by a plug or a wall made from an elastic material such as silicone, wherein it is possible to provide the plug or the wall in the region of the distal end of the sensor device.

Preferably, at least one sensor lumen is provided for an optically measuring fibre-based sensor which is as small as possible, e.g. for a pressure sensor of the Canadian company FISO Technologies. Such sensors can have a diameter in the region of only 200 μm or even less. They require neither a water column nor a separate holding plate. They are made for example from a glass material and can be of a biocompatible construction. The pressure sensor itself is preferably arranged on the tip of the sensor device. Differences in pressure or changes in pressure can be recorded very quickly and with good accuracy.

Preferably, the pressure sensor lumen has a diameter in the range of 0.3 to 0.8 mm, preferably 0.4 to 0.7 mm, particularly preferably 0.5 to 0.6 mm, in particular 0.55 mm.

According to a preferred embodiment, the fibre optic pressure sensor has a distal end which is arranged at a distance of a maximum of 5 cm, preferably a maximum of 3 cm, more preferably a maximum of 1 cm from a distal end of the perfusion cannula. This enables the pressure measurement to be carried out at a point which can be specified by the position of the distal end of the perfusion cannula. Optionally, a lateral feedthrough through the cannula wall can occur, e.g. as in the case of feedthroughs for the electrical lines for annular electrodes.

According to a preferred embodiment, at least one of the at least one sensor device is embedded in fluid-tight manner in the corresponding sensor lumen, in particular in the region of a distal end of the sensor device, preferably also in the region of a proximal end of the sensor device. This can ensure that the sensor device does not slip or become twisted in the perfusion cannula. Furthermore, the sensor lumen/lumina also do not need to be sterilised before each use. The embedding can consist for example of silicone, silicone-polyurethane copolymer, PVC and/or polyurethane. A sealing effect can be ensured here by the embedding itself.

According to a preferred embodiment, the perfusion cannula has a wire reinforcement which is preferably arranged radially outside of the at least one sensor lumen. As a result, the perfusion cannula can be given a relatively high (kink) stability and the risk of the perfusion cannula fracturing as a result of too great a bending can be reduced. A wire reinforcement is expedient in the case of materials and cannulas, respectively, with a lower kink stability.

The wire reinforcement preferably extends from a proximal end of the perfusion cannula to an annular electrode or to a first electrode from the perspective of the operator or surgeon, respectively, which is arranged within the cannula wall. The cannula wall more preferably has the wire reinforcement wound around it and is then provided with a coating. The wire reinforcement here is preferably completely embedded, in particular in a polymer.

According to a preferred embodiment, the perfusion cannula is covered by a coating of polyurethane. This can improve the gliding properties of the perfusion cannula in a vessel and in an artery or vein, respectively. The inner surface of a sensor lumen is preferably also provided with a coating, in particular polyurethane. The perfusion cannula preferably has an inner coating of polyurethane around which a wire reinforcement is provided, which is surrounded by an outer coating of polyurethane. The polyurethane material here can also be substituted by silicone, silicone-polyurethane copolymer or PVC.

The perfusion cannula is preferably covered with further coatings, in particular polyurethane coatings or coatings of silicone, silicone-polyurethane copolymer or PVC. A wire reinforcement is preferably also covered by at least one further coating.

According to a preferred embodiment, the perfusion cannula substantially consists of silicone, silicone-polyurethane copolymer, PVC, polyurethane (PU) and/or stainless VA steel. As a result, it is possible to ensure good flexibility and durability.

The cannula wall is preferably constructed in one piece, i.e. from an integral body of the same material apart from any coatings. This enables the provision of a robust perfusion cannula which can be subjected to a load in at least virtually the same manner in all spatial directions. It is furthermore possible to ensure that there are no cavities in which gas could be enclosed, which could result in the risk of an embolism.

The perfusion lumen and the sensor lumen/lumina are preferably incorporated in solid material and integrated in the cannula wall. This enables the provision of a perfusion cannula which can be handled easily and can be constructed with a cylindrical outer lateral surface.

According to a preferred embodiment, the perfusion cannula has a free operating lumen in which an operating probe, e.g. a diagnostic device in the form of a diagnostic catheter, can be arranged. This can further broaden the functionality of the perfusion cannula. A free operating lumen here is a type of operating channel in which it is optionally, in particular on the basis of particular applications, possible to incorporate for example a diagnostic device. The operating lumen can be provided as required by a customer and optionally also have an operating probe already arranged or embedded therein. However, the operating lumen is initially free, i.e. empty without any device arranged therein. The operating lumen preferably has a diameter of 1 to 6 French (Fr) corresponding to 0.35 to 2 mm, more preferably 4 Fr corresponding to 1.35 mm. The operating lumen can be sealed off with respect to the distal end of the perfusion cannula by means of a valve. The operating lumen can be constructed as a collapsible lumen and have a non-functioning mandrel. A collapsible lumen is a lumen which can be pushed to the side by a dilator of the cannula as the cannula is inserted and which can unfold as the dilator is removed. A mandrel is a placeholder which can be arranged in an operating lumen in order to close and fill this operating lumen when the operating lumen is not being used. The mandrel can thereby prevent the operating lumen from clotting. The mandrel can also consist of a long plastic blank which has an external diameter corresponding to the internal diameter of the operating lumen.

Preferably, the perfusion cannula has at least three lumina of which two are constructed as sensor lumina with a sensor device arranged therein and one lumen is constructed as an operating lumen with the operating probe arrangeable therein, wherein the lumina can be arranged concentrically and at the same spacing from one another around the central longitudinal axis of the perfusion cannula.

A perfusion cannula according to the invention can be part of a system which has an evaluating unit. Preferably, a perfusion cannula according to the invention for arterial access and a drainage cannula are provided in the system, in particular a circulation support system, whereby the system has an evaluating unit for evaluating measured values of at least one of the in each case at least one sensor device of the perfusion cannula according to the invention.

The system preferably has an arterial perfusion cannula for supplying a fluid and a venous perfusion cannula for removing a fluid. Thereby, for example, an ECG measurement can be carried out with one of the perfusion cannulas and a pressure measurement can be carried out with another of the perfusion cannulas. Optionally, in both cases a pressure measurement and an ECG measurement can be carried out, i.e. in each case at two different points of the body of the patient. Preferably, an ECG measurement is carried out arterially. Preferably, the arterial perfusion cannula is designed to be inserted into a groin region of a patient and to be advanced as far as the heart of the patient and has an insertion length which is in the range of 25 to 60 cm, preferably greater than 45 cm.

The system, especially a lung support system, can also have for example an oxygenator by means of which oxygen can be added to a fluid or blood supplied to the patient.

By means of a perfusion cannula according to the invention a patient can be examined or treated in particular in the following manner:

Firstly, an access is placed in a groin region of the patient. Then the perfusion cannula is inserted through an artery as far as the heart of the patient. Thereafter, the perfusion lumen is opened and a fluid supplied. At the same time as the fluid is supplied, an ECG measurement and/or a blood pressure measurement can be carried out.

Figure 1:
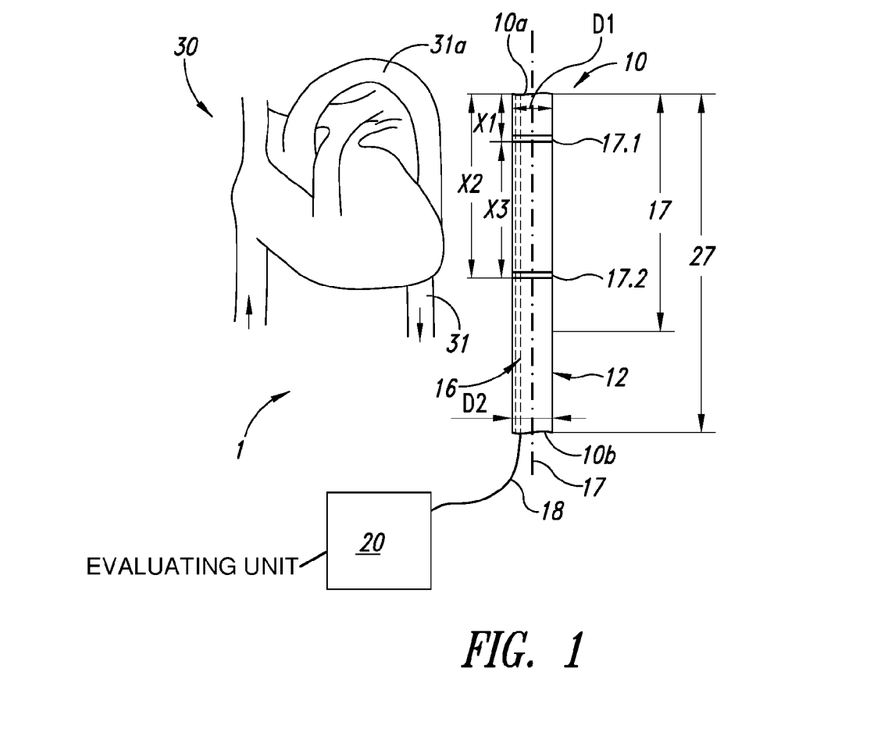
FIG. 1 is a schematic view of a lung support system with a schematically illustrated perfusion cannula according to an exemplary embodiment of the invention.

FIG. 1 shows a lung support system 1 having a perfusion cannula 10 which can be arranged in the region of the heart 30 of a patient, in particular in an aorta 31 near to an aortic arch 31$a$. The perfusion cannula 10 is coupled to an evaluating unit 20 by way of an electrical connection 18 and extends along a central longitudinal axis M. It has a distal end 10$a$ (cannula tip) and a proximal end 10$b$. The perfusion cannula 10 is divided into two portions, a distal insertion portion with an insertion length L1, and a proximal portion, which are together provided over a total length L2 of the perfusion cannula 10. The perfusion cannula 10 has a cannula wall 12 which has a diameter D2 in the region of the proximal end 10$b$ and a diameter D1 in the region of the distal end 10$a$. The diameter D1 is smaller than the diameter D2. The perfusion cannula 10 has a sensor lumen 16 (indicated by dashed lines) in which an electrical line is guided, by way of which annular electrodes 17.1, 17.2 are electrically contacted. The annular electrodes 17.1, 17.2 are arranged externally at the cannula wall 12. The distal electrode 17.1 is arranged at a distance x1 from the distal end 10$a$, whereby the distance x1 is for example in the region of 4 cm, and the proximal electrode 17.2 is arranged at a distance x2 from the distal end 10$a$, so that the electrodes are arranged at a distance x3 of approximately 40 to 60 mm from one another.

Figure 2:
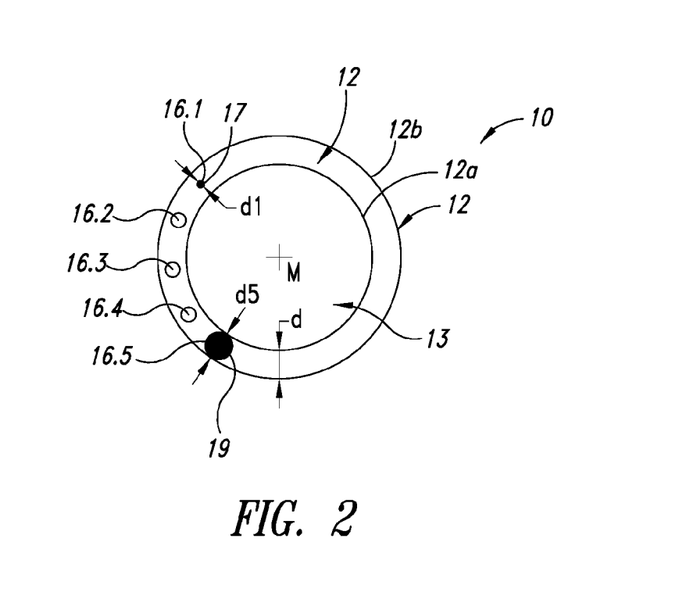
FIG. 2 is a schematic cross-sectional view of a perfusion cannula according to an exemplary embodiment of the invention.

FIG. 2 shows a perfusion cannula 10 having a cannula wall 12, wherein the cannula wall 12 has a cylindrical inner lateral surface 12$a$ and a cylindrical outer lateral surface 12$b$, and the cylindrical inner lateral surface 12$a$ surrounds a perfusion lumen 13. The lateral surfaces 12$a$, 12$b$ are arranged concentrically around a central longitudinal axis M. Five sensor lumina 16.1, 16.2, 16.3, 16.4, 16.5, which are arranged concentrically around the central longitudinal axis M, are integrated in the cannula wall 12. In a first of the sensor lumina 16.1 an ECG sensor 17 is embedded and in a fifth of the sensor lumina 16.5 a pressure sensor 19 is embedded. The cannula wall 12 has a wall thickness d which is in the region of 0.75 mm, and the first sensor lumen 16.1 has a diameter d1 which is in the region of 0.25 mm and the fifth sensor lumen 16.5 has a diameter d5 which is in the region of 0.55 mm.

Figure 3:
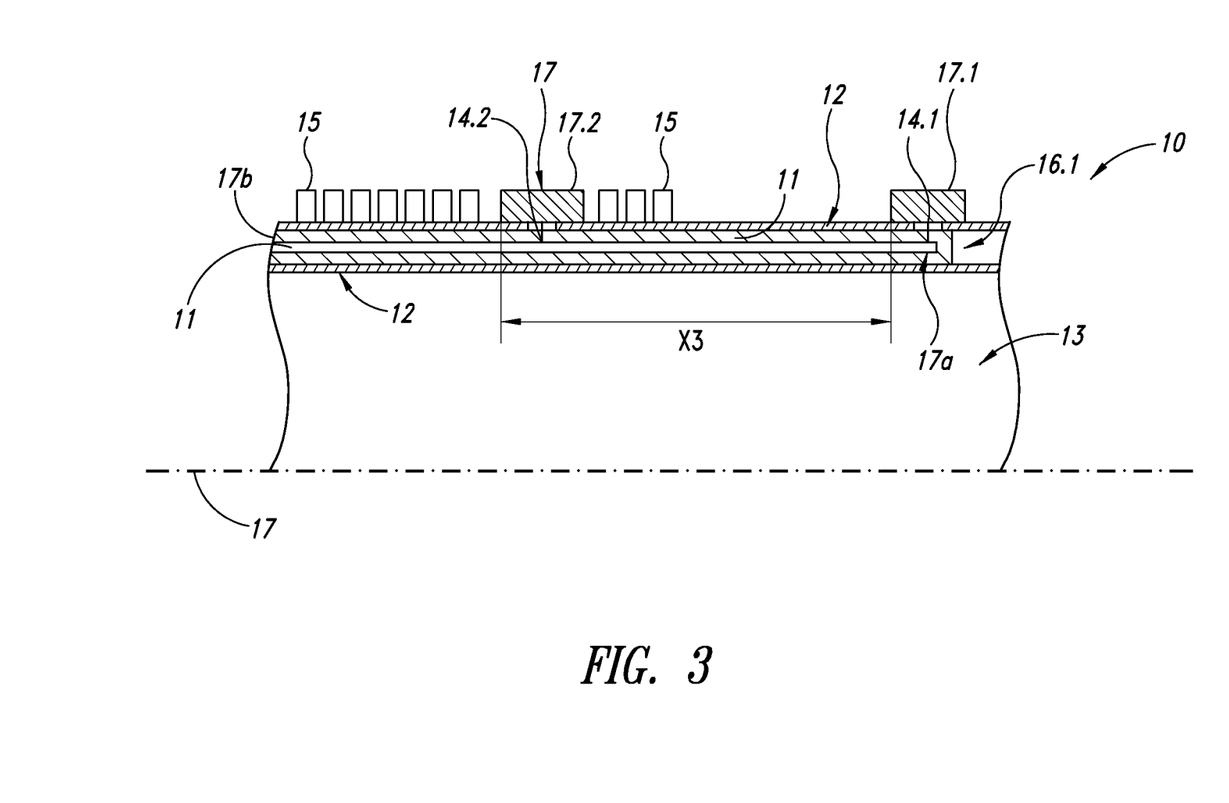
FIG. 3 is a schematic longitudinal section view of a perfusion cannula according to a further exemplary embodiment of the invention.

FIG. 3 shows a perfusion cannula 10 having a cannula wall 12 which surrounds a perfusion lumen 13. The perfusion cannula 10 extends along a central longitudinal axis M. A sensor lumen 16.1 for an ECG sensor 17 is integrated in the cannula wall 12, whereby the ECG sensor 17 is embedded in the sensor lumen 16.1 in an embedding 11 so that a distal end 17a of the ECG sensor 17 is enclosed by the embedding 11. The ECG sensor 17 has two annular electrodes 17.1, 17.2 which are arranged at a distance x3 from one another around the cannula wall 12. The annular electrodes 17.1, 17.2 are each connected to an electrical conductor 17b of the ECG sensor 17 by way of feedthroughs 14.1, 14.2. The annular electrodes 17.1, 17.2 cover the feedthroughs 14.1, 14.2. Furthermore provided externally around the cannula wall 12 is a wire reinforcement 15 which, starting from a proximal end of the perfusion cannula 10, is provided as far as the proximally arranged (second) annular electrode 17.2 and can optionally also be provided distally of the second annular electrode 17.2, as shown. To this end, the wire reinforcement 15 is preferably formed by two individual portions.

Figure 4:
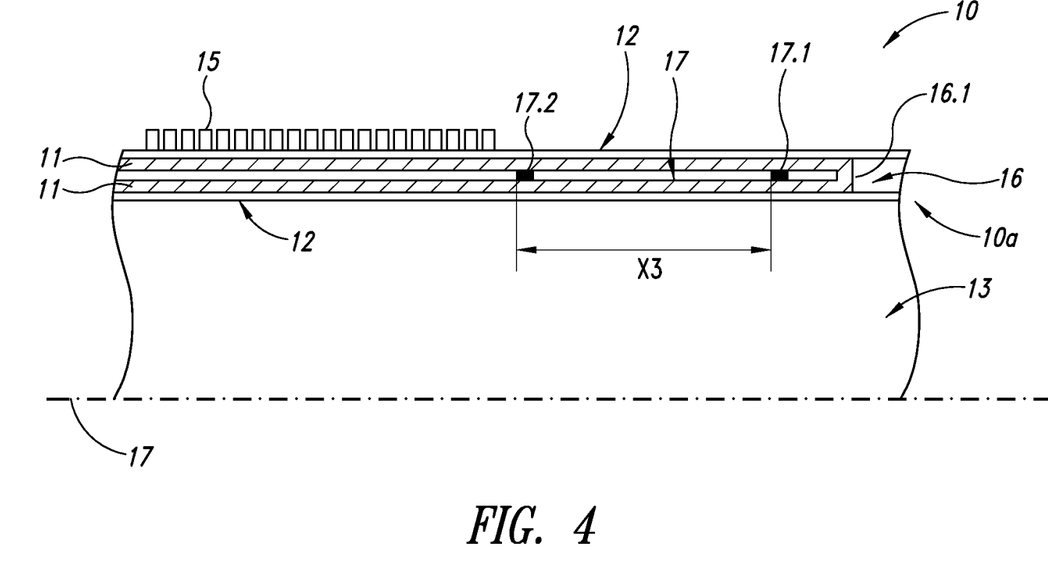
FIG. 4 is a schematic longitudinal section view of a perfusion cannula according to yet a further exemplary embodiment of the invention.

FIG. 4 shows a perfusion cannula 10 which, unlike the perfusion cannula 10 shown in FIG. 3, does not have annular electrodes but electrodes 17.1, 17.2 of an ECG sensor 17 which are arranged inside a sensor lumen 16.1. The ECG sensor 17 is arranged completely in an embedding 11 and is sealed-off (only) with respect to a distal end 10a of the perfusion cannula 10. The perfusion cannula 10 therefore has no feedthroughs and a wire reinforcement 15 is constructed in one piece and wound continuously around a cannula wall 12. Please refer to FIG. 3 for an explanation of the further reference numerals.

Figure 5:
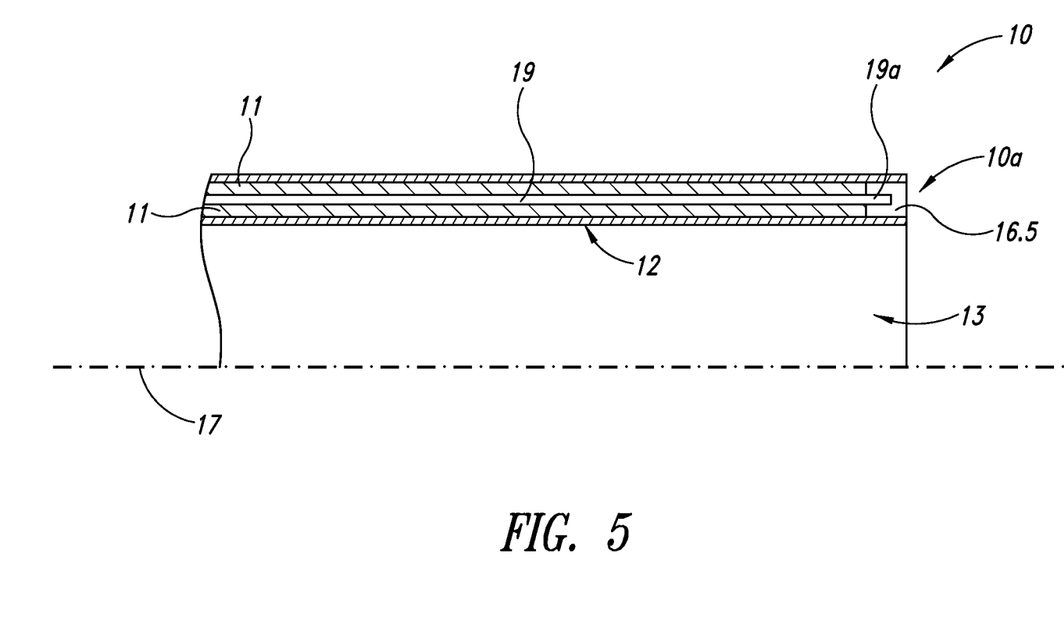
FIG. 5 is a schematic longitudinal section view of a perfusion cannula according to yet a further exemplary embodiment of the invention.

FIG. 5 shows a perfusion cannula 10 having a perfusion lumen 13 and having a sensor lumen 16.5, in which a pressure sensor 19 is embedded in an embedding 11 within a cannula wall 12, with a distal end 19a of the pressure sensor 19 protruding in distal direction from the embedding 11 in the region of a distal end 10a of the perfusion cannula 10. A pressure measurement can thereby take place in a fibre optical manner. In addition to the sensor lumen 16.5 and the pressure sensor 19 as shown in FIGS. 3 and 4, the perfusion cannula 10 can have a sensor lumen and an ECG sensor, respectively.

Figure 6:
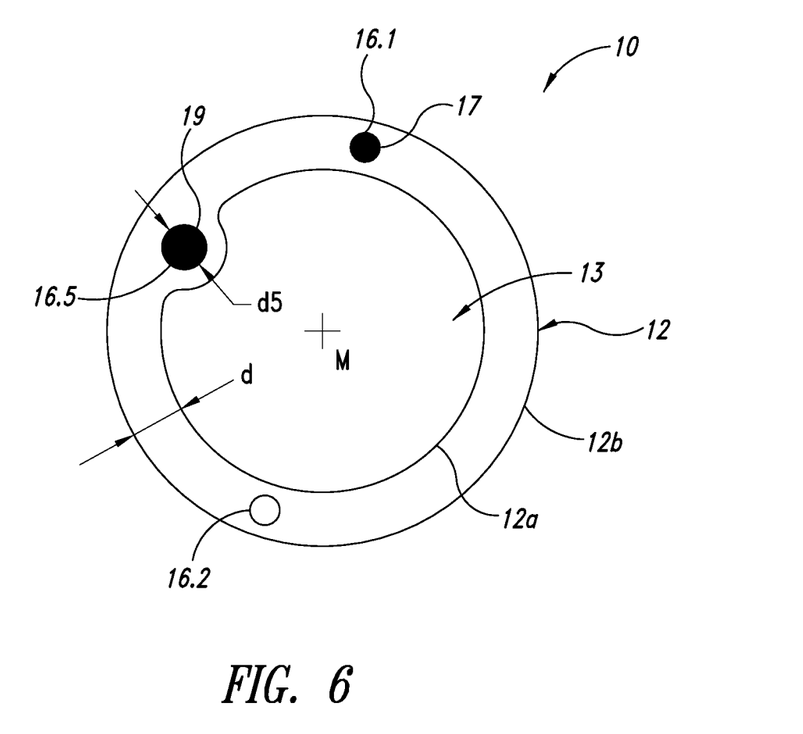
FIG. 6 is a schematic cross-sectional view of a perfusion cannula according to yet a further exemplary embodiment of the invention.

FIG. 6 shows a perfusion cannula 10 having a cannula wall 12, wherein the cannula wall 12 has an inner lateral surface 12a and a cylindrical outer lateral surface 12b, and the inner lateral surface 12a surrounds a perfusion lumen 13. The lateral surfaces 12a, 12b are arranged concentrically around a central longitudinal axis M. Integrated in the cannula wall 12 are three lumina 16.1, 16.2, 16.5, a first sensor lumen 16.1 with an ECG sensor 17 arranged therein and a fifth sensor lumen 16.5 with a pressure sensor 19 arranged therein and with a free operating lumen 16.2 in which an operating probe (not illustrated) is optionally arrangeable as required. As a result of the arrangement of the fifth sensor lumen 16.5 in an inwardly protruding part of the cannula wall 12, a wall thickness d of the cannula wall 12 can be constructed comparatively thin in relation to a diameter d5 of the fifth sensor lumen 16.5, in particular regarding a good flexibility of the perfusion cannula 10 even if a larger sensor lumen or operating lumen should be required.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

LIST OF REFERENCE NUMERALS

1 System, in particular lung support system
10 Perfusion cannula
10a Distal end of the perfusion cannula
10b Proximal end of the perfusion cannula
11 Embedding
12 Cannula wall
12a Inner side of the cannula wall, in particular inner lateral surface
12b Outer side of the cannula wall, in particular outer lateral surface
13 Perfusion lumen
14.1 (First) feedthrough through cannula wall
14.2 (Second) feedthrough through cannula wall
15 Wire reinforcement
16 Lumen
16.1 (First) lumen
16.2 (Second) lumen
16.3 (Third) lumen
16.4 (Fourth) lumen
16.5 (Fifth) lumen
17 Sensor device, in particular ECG sensor
17a Distal end of the sensor device
17b Electrical conductor
17.1 (First) electrode, e.g. annular electrode
17.2 (Second) electrode, e.g. annular electrode
18 Electrical connection to an evaluating unit
19 Further sensor device, in particular pressure sensor
19a Distal end of the further sensor device
20 Evaluating unit
30 Heart of a patient
31 Main artery (aorta)
31a Aortic arch
d Width of the cannula wall in the radial direction (wall thickness)
d1 Diameter of the first lumen
d5 Diameter of the fifth lumen
D1 External diameter of the perfusion cannula at the distal end
D2 External diameter of the perfusion cannula at the proximal end
M Central longitudinal axis of the perfusion cannula
L1 Insertion length of the perfusion cannula
L2 Total length of the perfusion cannula
x1 Distance of a first electrode from the distal end
x2 Distance of a second electrode from the distal end
x3 Distance of the electrodes from one another

The invention claimed is:

1. A perfusion cannula for placement of an access, having a cannula wall and a perfusion lumen which is surrounded by the cannula wall and in which a fluid flow can flow through the perfusion cannula, wherein the cannula wall has an at least approximately constant radius cylindrical continuous inner lateral surface and an at least approximately constant radius cylindrical continuous outer lateral surface, wherein both lateral surfaces are arranged concentrically with respect to a central longitudinal axis of the perfusion cannula, the perfusion cannula comprising at least one sensor lumen and at least one sensor device arranged at least partially in the sensor lumen, wherein the sensor lumen is integrated in the cannula wall, wherein the integrated sensor lumen has a diameter which is smaller than a thickness of the cannula wall, and wherein the sensor lumen is arranged at the cannula wall, protruding laterally in the radial direction.

2. A perfusion cannula according to claim 1 wherein the perfusion cannula has an insertion length of greater than 15 cm.

3. A perfusion cannula according to claim 2 wherein the perfusion cannula has an insertion length of greater than 20 cm.

4. A perfusion cannula according to claim 2 wherein the perfusion cannula has an insertion length of greater than 25 cm.

5. A perfusion cannula according to claim 2 wherein the perfusion cannula has an insertion length in the range of 25 to 50 cm.

6. A perfusion cannula according to claim 1 wherein the perfusion cannula has an external diameter of between 5 and 35 French in the region of a distal end of the perfusion cannula.

7. A perfusion cannula according to claim 6 wherein the perfusion cannula has an external diameter of between 12 and 25 French, in the region of a distal end of the perfusion cannula.

8. A perfusion cannula according to claim 1 wherein the sensor device is constructed as an ECG sensor and the sensor lumen has a diameter of between 0.05 and 2 mm.

9. A perfusion cannula according to claim 8 wherein the sensor device is constructed as an ECG sensor and the sensor lumen has a diameter of between 0.2 and 0.5 mm.

10. A perfusion cannula according to claim 1 wherein at least one of the at least one sensor device is constructed as an ECG sensor and has an annular electrode arranged externally around the cannula wall and, by way of a feed through in the cannula wall, is electrically contacted by means of an electrical conductor guided in the corresponding sensor lumen.

11. A perfusion cannula according to claim 1 wherein at least one of the at least one sensor device is constructed as an ECG sensor with two electrodes arranged within the sensor lumen.

12. A perfusion cannula according to claim 1 wherein at least one of the at least one sensor device is constructed as a pressure sensor.

13. A perfusion cannula according to claim 12 wherein the pressure sensor is constructed as a fibre optic pressure sensor.

14. A perfusion cannula according to claim 13 wherein the fibre optic pressure sensor has a distal end which is arranged at a distance of less than or equal to 5 cm from a distal end of the perfusion cannula.

15. A perfusion cannula according to claim 14 wherein the fibre optic pressure sensor has a distal end which is arranged at a distance of less than or equal to 3 cm from a distal end of the perfusion cannula.

16. A perfusion cannula according to claim 14 wherein the fibre optic pressure sensor has a distal end which is arranged at a distance of less than or equal to 1 cm from a distal end of the perfusion cannula.

17. A perfusion cannula according claim 1 wherein at least one of the at least one sensor device is embedded in fluid-tight manner in the corresponding sensor lumen.

18. A perfusion cannula according claim 17 wherein at least one of the at least one sensor device is embedded in fluid-tight manner in the corresponding sensor lumen in the region of a distal end of the sensor device.

19. A perfusion cannula according to claim 1 wherein the perfusion cannula has a wire reinforcement which is arranged radially outside of the at least one sensor lumen.

20. A perfusion cannula according to claim 1 wherein the perfusion cannula is covered with a polyurethane coating.

21. A perfusion cannula according to claim 1 wherein the perfusion cannula comprises silicone, silicone-polyurethane copolymer, PVC, polyurethane, or stainless VA steel.

22. A perfusion cannula according to claim 1 wherein the perfusion cannula has a free operating lumen in which an operating probe can be arranged.

23. A perfusion cannula according to claim 1 wherein the sensor lumen is arranged protruding inwardly into the perfusion lumen.

24. A circulation support system, having a perfusion cannula according to claim 1 for arterial access and having an evaluating unit for evaluating measured values of at least one of the in each case at least one sensor device of the perfusion cannula.

* * * * *

UNITED STATES PATENT AND TRADEMARK OFFICE
CERTIFICATE OF CORRECTION

PATENT NO. : 9,717,434 B2  
APPLICATION NO. : 14/338213  
DATED : August 1, 2017  
INVENTOR(S) : Gorhan et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 237 days.

Signed and Sealed this  
Thirtieth Day of January, 2018

Joseph Matal  
*Performing the Functions and Duties of the*  
*Under Secretary of Commerce for Intellectual Property and*  
*Director of the United States Patent and Trademark Office*